(12) United States Patent
Eddington et al.

(10) Patent No.: US 7,300,787 B2
(45) Date of Patent: Nov. 27, 2007

(54) LACTOBACILLUS STRAINS AND USE THEREOF IN FERMENTATION FOR L-LACTIC ACID PRODUCTION

(75) Inventors: John M. Eddington, Mt. Zion, IL (US); Kevin Brent Johnson, Mt. Zion, IL (US); Hungming J. Liaw, Champaign, IL (US); Melanie Rowe, Appleton, WI (US); Yuegin Yang, Decatur, IL (US)

(73) Assignee: Archer-Daniels-Midland Company, Decatur, IL (US)

( * ) Notice: Subject to any disclaimer, the term of this patent is extended or adjusted under 35 U.S.C. 154(b) by 438 days.

(21) Appl. No.: 10/189,193

(22) Filed: Jul. 5, 2002

(65) Prior Publication Data

US 2004/0005677 A1    Jan. 8, 2004

(51) Int. Cl.
*C12P 7/56* (2006.01)
*C12N 1/21* (2006.01)

(52) U.S. Cl. ............... 435/252.9; 435/139; 435/252.3
(58) Field of Classification Search ............ 435/252.9, 435/139, 252.3
See application file for complete search history.

(56) References Cited

U.S. PATENT DOCUMENTS

| | | | |
|---|---|---|---|
| 1,995,970 A | 3/1935 | Dorough | |
| 2,362,511 A | 11/1944 | Teeters | |
| 2,683,136 A | 7/1954 | Higgins | |
| 3,636,956 A | 1/1972 | Schneider | |
| 3,797,499 A | 3/1974 | Schneider | |
| 3,987,028 A * | 10/1976 | Lunel et al. ................ | 536/6.4 |
| 4,440,792 A | 4/1984 | Bradford et al. | |
| 4,521,434 A | 6/1985 | Matrozza | |
| 4,769,329 A * | 9/1988 | Cooper et al. .............. | 435/139 |
| 4,839,281 A | 6/1989 | Gorbach et al. | |
| 4,885,247 A | 12/1989 | Datta | |
| 4,963,486 A | 10/1990 | Hang | |
| 5,142,023 A | 8/1992 | Gruber et al. | |
| 5,147,668 A | 9/1992 | Munk | |
| 5,210,296 A | 5/1993 | Cockrem et al. | |
| 5,219,597 A | 6/1993 | Mok et al. | |
| 5,234,826 A | 8/1993 | Yamagami et al. | |
| 5,247,058 A | 9/1993 | Gruber et al. | |
| 5,247,059 A | 9/1993 | Gruber et al. | |
| 5,250,182 A | 10/1993 | Bento et al. | |
| 5,258,488 A | 11/1993 | Gruber et al. | |
| 5,274,073 A | 12/1993 | Gruber et al. | |
| 5,296,221 A | 3/1994 | Mitsuoka et al. | |
| 5,324,515 A | 6/1994 | Lee et al. | |
| 5,338,682 A | 8/1994 | Sasaki et al. | |
| 5,338,822 A | 8/1994 | Gruber et al. | |
| 5,357,035 A | 10/1994 | Gruber et al. | |
| 5,359,026 A | 10/1994 | Gruber | |
| 5,378,458 A | 1/1995 | Mayra-Makinen et al. | |
| 5,416,020 A | 5/1995 | Severson et al. | |
| 5,446,123 A | 8/1995 | Gruber et al. | |
| 5,464,760 A | 11/1995 | Tsai et al. | |
| 5,475,080 A | 12/1995 | Gruber et al. | |
| 5,482,723 A | 1/1996 | Sasaki et al. | |
| 5,484,881 A | 1/1996 | Gruber et al. | |
| 5,503,750 A | 4/1996 | Russo, Jr. et al. | |
| 5,510,526 A | 4/1996 | Baniel et al. | |
| 5,525,706 A | 6/1996 | Gruber et al. | |
| 5,536,807 A | 7/1996 | Gruber et al. | |
| 5,539,081 A | 7/1996 | Gruber et al. | |
| 5,547,692 A | 8/1996 | Iritani et al. | |
| 5,585,191 A | 12/1996 | Gruber et al. | |
| 5,594,095 A | 1/1997 | Gruber et al. | |
| 5,707,854 A * | 1/1998 | Saito et al. ............... | 435/252.9 |
| 5,763,513 A | 6/1998 | Suzuki et al. | |
| 5,798,237 A | 8/1998 | Picataggio et al. | |
| 5,801,025 A | 9/1998 | Ohara et al. | |
| 5,814,498 A | 9/1998 | Mani et al. | |
| 5,849,565 A | 12/1998 | Ehret | |
| 6,180,599 B1 * | 1/2001 | Min ............................ | 514/8 |
| 6,187,951 B1 | 2/2001 | Baniel et al. | |
| 6,229,046 B1 | 5/2001 | Eyal et al. | |
| 6,280,985 B1 | 8/2001 | Caboche et al. | |
| 6,290,896 B1 | 9/2001 | Suzuki et al. | |
| 6,319,382 B1 | 11/2001 | Norddahl | |

* cited by examiner

*Primary Examiner*—Chih-Min Kam
(74) *Attorney, Agent, or Firm*—Kirckpatrick & Lockhart Preston Gates Ellis LLP (57) ABSTRACT

The present invention relates to L-lactic acid producing bacterial strains, including *Lactobacilli* such as NRRL B-30568 (ADM B64), NRRL B-30569 (ADM DEC2-2B), NRRL B-30570 (ADM RP1A-4E), NRRL B-30571 (ADM RP2-1C), NRRL B-30572 (ADM RP3-1E), NRRL, B-30573 (ADM RP4A-2C), NRRL B-30574 (ADM LC49.25), NRRL B-30575 (ADM LC54.62) and mutations thereof. The present invention also relates to processes of producing L-lactic acid by culturing these strains. The present invention also relates to a method of making a bacterial strain that is capable of producing an increased yield or optical purity of L-lactic acid relative to these strains.

18 Claims, 2 Drawing Sheets

Figure 1. Riboprint ® Pattern of isolated *Lactobacillus* strains

NRRL B-30568 (ADM B6-4)

ADM LC11-171

ADM LC15.7

ADM LC40-120

ADM LC45-8

NRRL B-30574 (ADM LC49.25)

NRRL B-30575 (ADM LC54.62)

FIG. 2.

The development of strains producing homogeneous L-lactic acid

US 7,300,787 B2

LACTOBACILLUS STRAINS AND USE THEREOF IN FERMENTATION FOR L-LACTIC ACID PRODUCTION

BACKGROUND OF THE INVENTION

1. Field of the Invention

The invention relates to the isolation and mutation of bacterial strains that produce L-lactic acid. The invention also relates to the isolation and mutation of *Lactobacillus* strains for the production of L-lactic acid, fermentation media and procedures for producing L-lactic acid.

2. Related Art

Lactic acid, $CH_3CH(OH)CO_2H$, possesses one chiral carbon and thus can be present in the L- or D-stereoisomeric form. L-Lactic acid (also known as (S)-(+)-lactic acid) in optical purity does not contain any of its enatiomeric pair, D-lactic acid (or, (R)-(−)-lactic acid). As discussed throughout the description, L-lactic acid is interchangeable with S-lactic acid or (+)-lactic acid; D-lactic acid is interchangeable with R-lactic acid or (−)-lactic acid.

Optically pure L-lactic acid has several important industrial applications. U.S. Pat. No. 5,801,025 indicates that L-lactic acid has found its application in various fields including food and pharmaceuticals, brewing, tanning and optical materials. The pesticidal toxin produced by the bacteria of the present invention has attracted attention because it, unlike conventionally used agricultural chemicals, is harmless to humans and animals. U.S. Pat. No. 5,801,025 has also revealed that optically pure L-lactic acid is useful as liquid crystals, and is the preferred stereoisomeric form to be fed to infants.

U.S. Pat. No. 6,229,046 also describes that lactic acid currently used in food applications has chiral purity requirements greater than 95% chiral purity, generally with a preference for the "L" form. The chiral purity of lactic acid is also important for end products such as pharmaceuticals and other medical devices where lactic acid is a starting material.

U.S. Pat. No. 5,801,025 also describes the need for optically pure lactic acid when used as the starting material in the production of polylactic acid, a biodegradable substitute for other polymeric plastics. For example, the higher the optical purity of the starting lactic acid, the higher the degree of crystallization of the polymer produced. The polylactic acid with a high degree of crystallization is suitably used for stretched films and fibers.

U.S. Pat. No. 6,229,046 also indicates that the chiral purity of the lactic acid has a strong influence on the properties of the polymer. U.S. Pat. No. 5,484,881 describes how the crystallinity of polymers of lactic acid requires relatively long sequences of a particular stereoisomer, either long sequences of (R) or of (S) form. The length of the interrupting sequences may be important for establishing other features of the polymer, such as the rate at which it crystallizes, the melting point of the crystalline phase, or melt processability. Further discussion of the importance of optically pure lactic acid or its industrial use can be found, for example, in U.S. Pat. Nos. 5,142,023; 5,338,822; 5,536,807; and 5,585,191.

Lactic acid is widely recognized to be useful as a starting material for producing polylactic acid, a biodegradable plastic that has both environmental and medical advantages. Biodegradable polymers of lactic acid are less harmful to the environment than non-biodegradable polymers in that they more readily decompose. Such biodegradable polymers have also been useful in various medical applications. For example, sutures made of fibers of lactic acid polymers can be bioabsorbed by patients undergoing surgery. Processes of preparing lactic acid and polymers thereof can be found, for example, in U.S. Pat. Nos. 1,995,970; 2,362,511; 2,683,136; 3,636,956; 3,797,499; 5,801,025; 5,142,023; 5,247,058; 5,258,488; 5,357,035; 5,338,822; 5,446,123; 5,539,081; 5,525,706; 5,475,080; 5,359,026; 5,484,881; 5,585,191; 5,536,807; 5,247,059; 5,274,073; 5,510,526; 5,594,095; 5,763,513 and 6,290,896; all of which are herein incorporated by reference.

Methods of producing lactic acid via fermentation processes are described in U.S. Pat. Nos. 4,521,434; 4,839,281; 4,885,247; 4,963,486; 5,147,668; 5,210,296; 5,219,597; 5,234,826; 5,250,182; 5,296,221; 5,324,515; 5,338,682; 5,378,458; 5,416,020; 5,464,760; 5,482,723; 5,503,750; 5,547,692; 5,798,237; 5,801,025; 5,814,498; 5,849,565; 6,187,951; 6,229,046; 6,280,985 and 6,319,382; all of which are incorporated by reference.

The present invention improves upon these methods by providing lactic acid producing bacteria useful in fermentation processes whereby higher yields and greater optical purity of L-lactic acid are achieved. It is to be understood that both the foregoing general description and the following detailed description are exemplary and explanatory only and are intended to provide further explanation of the invention as claimed.

BRIEF SUMMARY OF THE INVENTION

The present invention relates to L-lactic acid producing bacterial strains. Preferably, the bacterial strains include NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62) and mutations thereof. The present invention also relates to processes of producing L-lactic acid by culturing these strains. The present invention also relates to a method of making a bacterial strain that is capable of producing an increased yield or optical purity of L-lactic acid relative to these strains.

DETAILED DESCRIPTION OF THE INVENTION

The present invention is directed to the identification, isolation and use of L-lactic acid producing bacterial strains.

Lactic acid producing bacterial strains include *Lactobacillus* strains as well as other bacterial strains having the identifiable characteristic of generating high yields of lactic acid. Yields are preferably higher than 90%, more preferably above 95%. Preferably lactic acid concentrations are in excess of 60, 70, 80 or 90 g/L of culture, more preferably in concentrations in excess of 100 g/L of culture.

Preferably, the bacterial strains of the present invention are capable of growing under fermentation conditions with greater than 60 g/L of lactic acid or a salt thereof.

The present invention is concerned with such bacterial strains that are capable of producing high yields of optically pure L-lactic acid. Preferably, bacterial strains of the present invention generate at least or greater than 90%, 91%, 92%, 93%, 94%, 95%, 96%, 97%, 98% or 99% optically pure L-lactic acid. Most preferably, the bacterial strains of the present invention produce 100% optically pure L-lactic acid.

As used herein, L-lactic acid that is "optically pure" or "100% optically pure" means L-lactic acid that is free from contamination by any of its D-lactic acid enantiomer. The degree of optical purity of an L-lactic acid sample is a reflection of the amount of D-lactic acid impurity present. If, for example, the total lactic acid content produced by a bacterial strain of the present invention is said to be 98% L-lactic acid, that means the remaining 2% of the lactic acid sample is the enantiomeric form, D-lactic acid.

In one embodiment, the present invention is directed to an essentially biologically pure culture of a microorganism strain having the identifying characteristics of a strain selected from the group consisting of NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62) and mutants of such strains that retain the ability to produce L-lactic acid in at least 90% or greater optical purity, under conditions that allow the production of L-lactic acid by such strains. The microorganism strains of the present embodiment are capable of producing L-lactic acid by fermentation in pure culture, i.e., in the absence of one or more additional microorganism strain(s).

Figure 1:
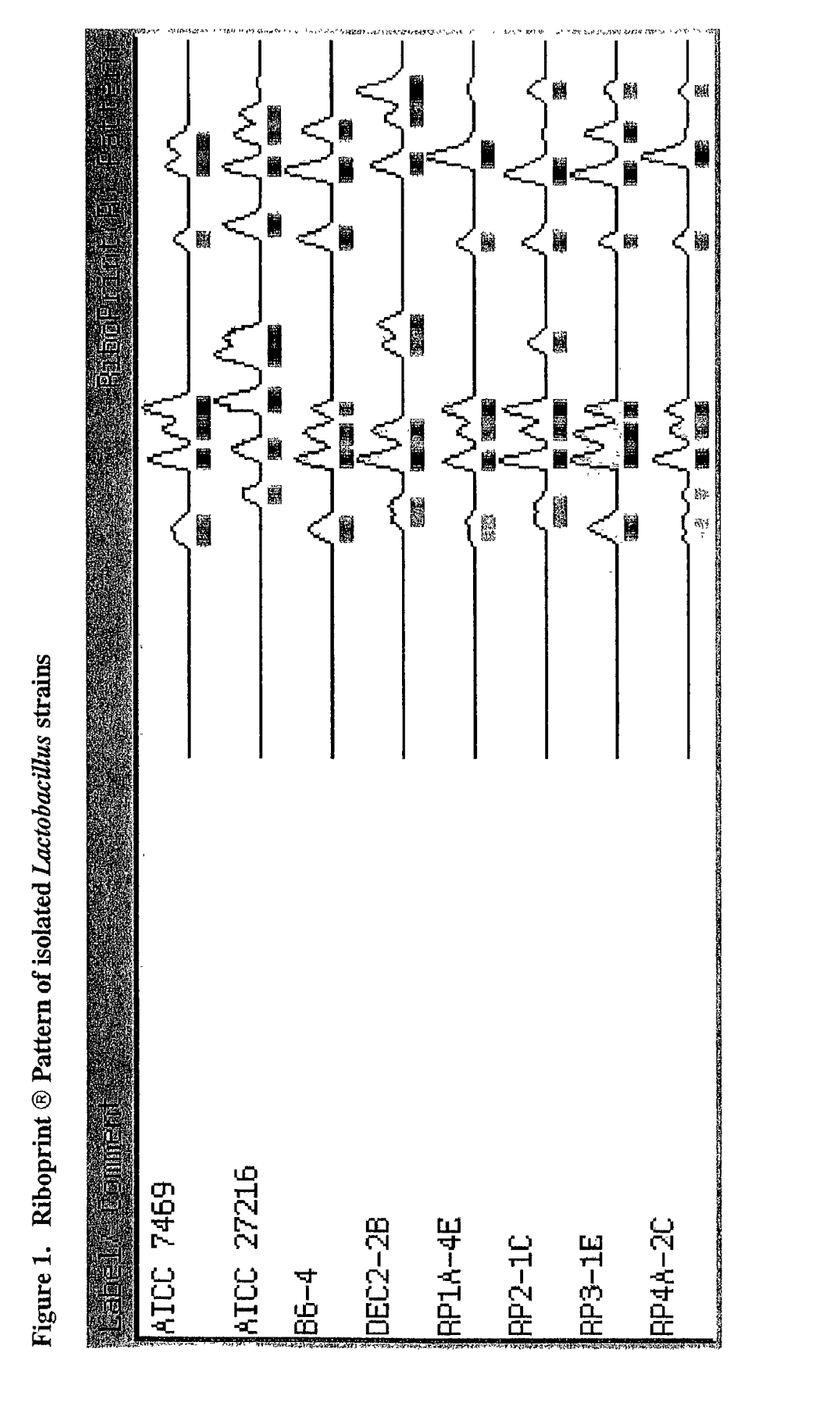
FIG. 1 is a depiction of RiboPrint® patterns of isolated *Lactobacillus* strains capable of producing large yields of optically pure L-lactic acid. RiboPrint® patterns were obtained from the following *Lactobacillus* strains: NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), and NRRL B-30573 (ADM RP4A-2C).

Strains NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62) were deposited at the Agricultural Research Service Culture Collection (NRRL), 1815 North University Street, Peoria, Ill. 61604, U.S.A., on Apr. 9, 2002 under the provisions of the Budapest Treaty. The characteristics of these Lactobacilli strains include:

(1) Cell Morphology: gram positive, non-spore forming rod bacteria; small rods appear singly or in pairs and form filaments in old culture;
(2) Colony Morphology: no pigment production; all grow to white smooth round colonies on Difco®® MRS agar plate and may form irregular edge when they age;
(3) Motility: non-motile;
(4) Temperature Range: optimal growth is 37°-43° C.;
(5) pH Range: optimal growth is between pH 5.5-6.0;
(6) Physiological Characteristics:
  (a) catalase: negative;
  (b) facultative anaerobic;
  (c) homofermentative from glucose with L-lactic acid as the major product;
  (d) at least half of end product is lactate, which is not fermented;
(7) Cultural Characteristics: requires complex nutrients such as amino acids, peptides, nucleic acid derivatives, vitamins, salts, and fermentable carbohydrates (see Table 2); and (8) RiboPrint® Analysis: RiboPrint® analysis involves hybridization of radio-labeled anti-sense RNA to the genetic material being studied, followed by detection of the labeled double-stranded hybrid using gel electrophoresis. The patterns obtained by this method are useful for differentiating not only between organisms of different species, but also between different strains of the same species. RiboPrinto patterns obtained for strains NRRL B-30568 (ADM B6-4), NRRL B-30569 (ADM DEC2-2B), NRRL B-30570 (ADM RPIA-4E), NRRL B-30571 (ADM RP2-1C), NRRL B-30572 (ADM RP3-1E), and NRRL B-30573 (ADM RP4A-2C) are depicted in FIG. 1.

The present invention is also directed to a process for producing L-lactic acid comprising (a) culturing a bacterial strain capable of producing L-lactic acid in at least 90% or greater optical purity when compared to the total lactic acid content, under conditions that allow for the production of such L-lactic acid; and (b) producing the L-lactic acid. The process also relates to extracting and isolating the L-lactic acid from the host cell.

Preferably, the process for producing L-lactic acid comprises culturing a bacterial strain selected from the group consisting of NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62) and mutants of such strains that retain the ability to produce L-lactic acid in at least 90% or greater optical purity, under conditions that allow the production of L-lactic acid by such strains.

In another aspect, the invention relates to a method of producing a bacterial strain that is capable of synthesizing L-lactic acid in a higher amount or yield or optical purity than a starting strain. Such a method comprises: (a) inoculating bacterial growth medium with a starting strain selected from the group consisting of NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62) and mutants of such strains that retain the ability to produce L-lactic acid in at least 90% or greater optical purity, under conditions that allow the production of L-lactic acid by such strains; (b) incubating the strain in such medium thereby creating a population of mostly identical bacteria; (c) harvesting such population during the mid-log phase of its exponential growth; (d) resuspending such population in a buffer and subjecting it to mutagenic conditions or to a mutagen; (e) isolating from the population one or more individual mutant bacterial strains; (f) screening such mutant bacterial strains for improved yield or improved optical purity of L-lactic acid relative to the starting strain used to innoculate the bacterial growth medium in (a); (g) selecting one or more mutant bacterial strains which produce an improved yield or optical purity of L-lactic acid relative to the starting strain; and (h) optionally repeating (a) through (g) one or more times with such mutant bacterial strains having an improved yield or optical purity of L-lactic acid. Any chemical mutagen or physical mutagenic condition can be used. Preferably, the mutagen of this method is chemical. Most preferably it is N-methyl-N'-nitro-N-nitrosoguanidine (NTG) or the mutagen is a combination of ethyl methane sulfonate (EMS) and ultraviolet light (UV).

In another aspect of the invention, such isolating, screening or selecting of the mutant bacterial strains according to (e), (f) or (g) further comprises: (i) diluting and spreading a portion of the population of bacteria onto agar plates having selective growth medium comprising Bromocresol green; (j) incubating the plates; and (k) selecting from the plates bacterial colonies displaying a yellow halo. The screening of the mutant bacterial strains according to (f) can optionally further comprise: (l) respectively inoculating separate batches of liquid bacterial growth medium containing Bromocresol green with such individual mutant bacterial strains; (m) incubating the medium under fermentation conditions; and (n) selecting the mutant bacterial strains on the basis of the extent to which growth medium is turned yellow as a result of lactic acid being overproduced. Alternatively, the screening of the individual bacterial strains according to (f) can further comprise: (o) respectively inoculating separate batches of liquid bacterial growth medium with such individual mutant bacterial strains; (p) incubating the medium under fermentative conditions; and (q) selecting the mutant bacterial strains on the basis of the extent to which $CO_2$ gas is generated. Preferably, homofermentative lactic acid producing bacteria are selected that do not generate $CO_2$ gas.

Preferably, the processes of this invention comprise culturing a bacterial strain under fermentation conditions in a medium containing dextrose, corn steep liquor, soy flour, malt extract, molasses, soy protein, whey, cotton seed protein, yeast extract or other peptides or peptone as nutrient supplements. More preferably, the L-lactic acid produced by the process is at least or greater than about 90, 91, 92, 93, 94, 95, 96, 97, 98 or 99% optically pure when compared to the total lactic acid content. Most preferably, the L-lactic acid produced by the process is about 100% optically pure when compared to the total lactic acid content. It is also preferred that the bacterial strain is capable of growing under fermentation conditions in the presence of 60 g/L or more of lactic acid or a salt thereof.

Also preferably, the culturing can be done in a medium containing dextrose, glycerol, erythritol, D-arabinose, L-arabinose, ribose, D-xylose, L-xylose, adonitol, beta-methyl-D-xyloside, galactose, glucose, fructose, manose, sorbose, rhamnose, dulcitol, inositol, mannitol, sorbitol, alpha-methyl-D-mannoside, alpha-methyl-D-glucoside, n-acetyl-glucosamine, amygdalin, arbutin, esculin, salicin, cellobiose, maltose, lactose, melibiose, sucrose, trehalose, inulin, melezitose, raffinose, starch, glycogen, xylitol, gentiobiose, D-turanose, D-lyxose, D-tagatose, D-fucose, L-fucose, D-arabitol, L-arabitol, gluconate, 2-keto-gluconate, molasses, whey, or 5-keto-gluconate.

Another aspect of the invention relates to a method of identifying from sources of biological material bacterial strains capable of synthesizing at least or greater than about 90% optically pure L-lactic acid. Yields are preferably higher than 90%, more preferably above 95%. Preferably lactic acid concentrations are in excess of 60, 70, 80 or 90 g/L, more preferably in concentrations in excess of 100 g/L. Such a method comprises: (a) collecting a sample from a biological material; (b) inoculating a bacterial growth medium with such a sample and incubating the medium thereby propagating a mixed population of bacteria; (c) isolating from the mixed population of bacteria one or more individual bacterial strains; and (d) screening and identifying such one or more individual bacterial strains capable of synthesizing at least or greater than about 90% optically pure L-lactic acid. Such strains are used to produce L-lactic acid at least or greater than 90% optically pure. Preferably, the biological sample is corn steep liquor. The method of the present invention further comprises fermenting such one or more individual bacterial strains in growth medium containing corn steep liquor as a carbon source and thereafter extracting said L-lactic acid.

In another aspect of the invention, such isolating and screening of the individual bacterial strains according to (c) and (d) further comprises: (e) diluting and spreading a portion of the mixed population of bacteria onto agar plates having selective growth medium comprising Bromocresol green; (f) incubating the plates; and (g) selecting from the plates bacterial colonies displaying a yellow halo. The screening of the individual bacterial strains according to (d) can further comprise: (h) respectively inoculating separate batches of liquid bacterial growth medium containing Bromocresol green with such individual bacterial strains; (i) incubating the medium under fermentation conditions; and (j) selecting the bacterial strains on the basis of the extent to which growth medium is turned yellow as a result of lactic acid being overproduced. Alternatively, the screening of the individual bacterial strains according to (d) can further comprise: (k) respectively inoculating separate batches of liquid bacterial growth medium with such individual bacterial strains; (l) incubating the medium under fermentative conditions; and (m) selecting the bacterial strains on the basis of the extent to which $CO_2$ gas is generated.

Also preferably, the select bacterial strains of this method are capable of growing under fermentation conditions in the presence of 60 g/L or more of lactic acid or a salt thereof. Also preferably, the optical purity of the L-lactic acid produced by the select bacterial strains of this method is at least or greater than 91, 92, 93, 94, 95, 96, 97, 98 or 99%. Most preferably, the optical purity of the L-lactic acid produced by the select bacterial strains of this method is 100%.

Bacteria identified from biological material according to this method can also be mutated, as described above. Such mutation would produce a bacterial strain that is capable of synthesizing L-lactic acid in a higher amount or yield or optical purity than the starting strain newly identified from the biological material.

Preferably, the biological material of this method includes material from plants, animals, or microorganisms including bacteria, yeast or fungi. The plant product of this method can be derived from any part of a plant which produces corn, rice, wheat, barley, hops, milo or other grains, potatoes, yams, sweet potatoes or other tubers, soy or other beans, sugar cane, carrots, beets, bananas, plantains, apples, oranges, melons, grapes or other fruit, lettuce, cabbage, onions, carrots, beets, radishes or other roots, tomatoes, or accompanying soil thereof. Preferably, the biological material of this method includes corn mill plant soil or corn steep liquor. As described in U.S. Pat. No. 4,440,792, corn steep liquor is the first by-product of the corn wet-milling process. Biological material in liquid form, such as corn steep liquor, can be used directly for purposes of innoculating a bacterial growth medium. Alternatively, biological material in solid form, such as soil samples collected around corn processing or manufacturing plant sites (i.e., plant soil), are prepared as suspensions in sterile water prior to their use to innoculate the bacterial growth medium.

Corn steep liquor used as the source of bacteria is understood to mean nonsterilized, nonautoclaved or raw corn steep liquor. Such corn steep liquor may contain viable bacteria. In contrast, corn steep liquor used as a carbon or nitrogen source in a bacterial growth medium used to grow a culture of a particular bacterial strain must first be sterilized (e.g., autoclaved).

Lactic acid producing bacteria have been found in corn mill plants, products such as corn steep liquor, plants, processed plant waste products, dairy products, meat, animal waste products, water, sewage, beer, fruits, dirt and other sources. Samples from such sources are used to innoculate growth medium. Examples of useful growth medium are included, inter alia, in J. Sambrook et al., Molecular Cloning, A Laboratory Manual, 2d ed., Vol. 3, pages A.1-A.4, Cold Spring Harbor Laboratory Press (1989). A preferred growth medium comprises a carbohydrate source, ADM (Archer-Daniels-Midland Company) corn steep liquor added as a dry solid, calcium lactate, $MgSO_4 \cdot 7H_2O$, $MnSO_4 \cdot H_2O$, sodium acetate, $K_2HPO_4$, $KH_2PO_4$, and $CaCO_3$. Examples of useful carbohydrate sources are given in Table 2. These carbohydrates can be added to a final concentration of 50 to 150 g/L. $FeSO_4 \cdot 7H_2O$, uracil, and riboflavin are optionally added. Antifoam can be added during fermentation. Preferably, the pH of the medium is adjusted to 6.0 to 6.5 before autoclaving.

In one embodiment, the present invention is directed to bacterial strains capable of growing and thriving under acidic conditions having high concentrations of lactic acid or a lactate salt thereof. For example, calcium lactate is added to the medium to screen for bacteria within a sample capable of overproducing lactic acid. Preferably, bacteria that thrive and overproduce lactic acid in media already containing high levels of lactic acid are identified. When such bacteria are used to innoculate starting media having no lactic acid, the bacteria will continue to thrive and produce lactic acid even after generating and excreting large quantities of lactic acid during fermentation. Other lactate salts and hydrates thereof can also be added to the medium. Non-limiting examples of ionic counterparts which can form salts with lactate include lithium, sodium, potassium, magnesium, calcium, titanium, chromium, molybdenum, tungsten, manganese, iron, cobalt, nickle, copper, silver, gold, zinc, cadmium, aluminum, tin or lead each with the appropriate valency to form an ionic salt. In addition to atomic cationic counterparts, molecular cationic counterparts (for example, ammonium) can also form salts with lactate.

In addition to the above ingredients, selective growth medium preferably includes Bromocresol green. When lactic acid producing bacteria are cultured in this medium, the lactic acid produced causes the color of the medium to turn yellow. Hence, growth medium can be inoculated with a sample, for example, which contains *Laclobacillus* strains. A portion of this culture can be streaked onto plates having Bromocresol green. The *Lactobacilli* bacterial colonies will have yellow halos indicative of the formation of lactic acid. These strains can be further tested for their ability to produce high yields of optically pure L-lactic acid under fermentation conditions.

Other colorimetric pH indicators can also be used in the present invention. Examples of such indicators include, inter alia, Alizarin sulphonic acid (sodium salt), Methyl red (sodium salt), Chlorophenol red, Litmus, Bromocresol purple, Bromophenol red, 4-Nitrophenol, Bromoxylenol blue, Bromothymol blue, Phenol red, 3-Nitrophenol, Neutral Red, Brilliant green, Eosin yellowish, Erythrosine B, Methyl green, 2,2',2",4,4'-pentamethoxytri-phenyl carbinol, Eosin bluish, Quinaldine red, 2,4-Dinitro phenol, 4-(Dimethylamino)azobenzol, Bromochlorophenol blue, Bromophenol blue, Congo red, Methyl orange, 2,5-Dinitrophenol, and Chlorophenol red all of which are available from Merck and Co., Inc., Whitehouse Station, N.J.

Alternatively, changes in pH can be monitored using fluorometric assays. Examples of fluorometric dyes that can be used include, inter alia, 9-amino-6-chloro-2-methoxyacridine, 5-(and-6)-carboxy-2',7'-dichlorofluorescein, 5-(and-6)-carboxy-2',7'-dichlorofluorescein diacetate, Cl-NERF, DM-NERF, LysoSensor™ Blue, LysoSensor™ Green, LysoSensor™ Yellow/Blue, Oregon Green®, Rhodol Green™, 2',7'-bis-(2-carboxyethyl)-5-(and-6)-carboxyfluorescein, 2',7'-bis-(3-carboxypropyl)-5-(and-6)-carboxyfluorescein, 5-(and-6)-carboxyfluorescein, 5-(and-6)-carboxynaphthofluorescein, 5-(and-6)-carboxy SNAFL®-1, (5-chloromethylfluorescein diacetate), 8-hydroxypyrene-1, 3,6-trisulfonic acid, trisodium salt, nigericin, free acid, 1-(2-nitrophenyl)ethyl phosphate, diammonium salt, 5-sulfofluorescein diacetate, sodium salt all available from Molecular Probes, Inc., Eugene Oregon.

In the present invention, such strains are screened to ensure that they efficiently convert pyruvate to lactic acid instead of ethanol. Whereas homofermentative lactic acid producing bacteria do not generate $CO_2$ gas, heterofermentative lactic acid producing bacteria generate other products such as $CO_2$ gas and ethanol in addition to lactic acid. The conversion of pyruvate to ethanol involves the loss of $CO_2$. Accordingly, the extent of $CO_2$ gas generated during fermentation is an indication of the extent to which pyruvate is wastefully converted to ethanol. $CO_2$ can be detected by culturing lactic acid producing bacterial strains in inverted test tubes, for example, to observe formation of gas bubbles. Alternatively, the formation of $CO_2$ can be monitored by observing changes in pressure or its characteristic spectrum via IR or other spectroscopic technique. According to the present invention, preferably homofermentative lactic acid producing bacteria are selected.

The present invention is also directed to a method for improving such L-lactic acid producing bacterial strains that produce high yields of optically pure L-lactic acid by mutation of such strains. Such mutation results in the generation of new strains having improved properties. In particular, the improved properties include the production of higher yields or greater optical purity of L-lactic acid. Improvements can also include higher fermentation production rates of L-lactic acid; production of L-lactic acid with fewer byproducts; or production of L-lactic acid optimized for specific fermentation conditions including temperature, pH tolerance, or carbohydrate source. Although L-lactic acid producing bacterial strains can be useful without any mutation, these strains can also undergo mutation one or more times. Preferred bacterial strains to be mutated include NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), NRRL B-30575 (ADM LC54.62).

Mutation can be performed in any way that achieves the desired end. The skilled artisan is familiar with a wide variety of mutagenic techniques. Illustrative examples of suitable methods for preparing mutants of the inventive microorganism strains include, but are not limited to: mutagenesis by irradiation with ultraviolet light or X-rays, or by treatment with a chemical mutagen such as nitrosoguanidine (N-methyl-N'-nitro-N-nitrosoguanidine), methylmethanesulfonate, nitrogen mustard and the like; gene integration techniques, such as those mediated by insertional elements or transposons or by homologous recombination oftransforming linear or circular DNA molecules; and transduction mediated by bacteriophages. These methods are well known in the art and are described, for example, in J. H. Miller, *Experiments in Molecular Genetics*, Cold Spring Harbor Laboratory Press, Cold Spring Harbor, N.Y. (1972); J. H. Miller, *A Short Course in Bacterial Genetics*, Cold Spring Harbor Laboratory Press, Cold Spring Harbor, N.Y. (1992); M. Singer and P. Berg, *Genes & Genomes*, University Science Books, Mill Valley, Calif. (1991); J. Sambrook, E. F. Fritsch and T. Maniatis, *Molecular Cloning: A Laboratory Manual*, 2d ed., Cold Spring Harbor Laboratory Press, Cold Spring Harbor, N.Y. (1989); P. B. Kaufman et al., *Handbook of Molecular and Cellular Methods in Biology and Medicine*, CRC Press, Boca Raton, Fla. (1995); *Methods in Plant Molecular Biology and Biotechnology*, B. R. Glick and J. E. Thompson, eds., CRC Press, Boca Raton, Fla. (1993); and P. F. Smith-Keary, *Molecular Genetics of Escherichia coli*, The Guilford Press, New York, N.Y. (1989).

In one embodiment of the present invention, a bacterial growth is harvested during mid-log phase. The collected cells are suspended in buffer and treated with N-methyl-N-nitro-N-nitrosoguanidine (NTG). After an incubatory period, mutagenesis is stopped by washing the cells several times with fresh buffer (absent any NTG). Alternatively, a bacterial culture can be mutagenized with ultraviolet light (UV) and ethyl methane sulfonate (EMS). In this process, cells are first treated with EMS at a concentration of 25 µL/mL in 0.1 M phosphate buffer (pH 7.0) for an incubatory period, such as 30 minutes at 43° C. After washing several times with the same buffer, EMS treated cells can be irradiated with UV for 50 seconds.

Genetic analysis of isolated or mutated lactic acid producing bacteria can be performed using the RiboPrinter® Microbial Characterization System (Qualicon Inc., Delaware). RiboPrint® is an automated ribotyping system that generates and analyzes genetic fingerprints of bacteria. The genetic fingerprinting patterns are normalized digital representations of the genetic data for each sample. The patterns obtained by this method are useful for differentiating not only between organisms of different species, but also between different strains of the same species. Other techniques of differentiation can also be used and will be appreciated by the skilled artisan.

The present invention is also concerned with the production and purification of L-lactic acid using any of the lactic acid producing bacterial strains isolated or mutated by the present invention. Examples of fermentation techniques useful with the present invention are known to the skilled artisan. Recovery and purification of lactic acid from such fermentation processes are likewise known to the skilled artisan. Preferably, fermentation of waste products by lactic acid producing bacteria of the present invention is performed via batchwise processes.

A bacterial strain of the present invention can be cultured in a medium that comprises a carbon source and a nitrogen source. The carbon source can be various sugar alcohols, polyols, aldol sugars or keto sugars including but not limited to arabinose, cellobiose, fructose, glucose, glycerol, inositol, lactose, maltose, mannitol, mannose, rhamnose, raffinose, sorbitol, sorbose, sucrose, trehalose, pyruvate, succinate or methylamine or other substrates which may be determined by one skilled in the art. The medium preferably contains a polyol or aldol sugar, and even more preferably mannitol, inositol, sorbose, glycerol, sorbitol, lactose and arabinose as the carbon source at a concentration up to 20.0% by weight. Corn steep liquor can also serve as the carbon source. All of the carbon source may be added to the medium before the start of culturing, or it may be added step by step or continuously during culturing.

The medium used herein may be solid or liquid, synthetic or natural, and contains sufficient nutrients for the cultivation of the inventive microorganism strains. Preferably, the medium employed is a liquid medium, more preferably a synthetic liquid medium.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts useful in the culturing medium include, but are not limited to: salts of potassium, calcium, sodium, magnesium, manganese, iron, cobalt, zinc, copper, molybdenum, tungsten and other trace elements, and phosphoric acid.

Illustrative examples of appropriate trace nutrients, growth factors, and the like useful in the culturing medium include, but are not limited to: coenzyme A, pantothenic acid, pyridoxine-HCl, biotin, thiamine, riboflavin, flavine mononucleotide, flavine adenine dinucleotide, DL-6,8-thioctic acid, folic acid, Vitamin $B_{12}$, other vitamins, amino acids such as cysteine and hydroxyproline, bases such as adenine, uracil, guanine, thymine and cytosine, sodium thiosulfate, p- or r-aminobenzoic acid, niacinamide, nitriloacetate, and the like, either as pure or partially purified chemical compounds or as present in natural materials. Cultivation of the inventive microorganism strain may be accomplished using any of the submerged fermentation techniques known to those skilled in the art, such as airlift, traditional sparged-agitated designs, or in shaking culture.

The culture conditions employed, including temperature, pH, aeration or anaerobic sparging rate, agitation rate, culture duration, and the like, may be determined empirically by one of skill in the art to maximize production of L-lactic acid from bacteria of the present invention.

L-lactic acid that has accumulated in the cells and/or culture broth is isolated according to any of the known methods including ion exchange chromatography, gel filtration, solvent extraction, affinity chromatography, or any combination thereof. Any method that is suitable with the conditions employed for cultivation may be used.

The chemical yield of lactic acid can be assessed using high pressure liquid chromatography (HPLC). Alternatively, lactate analysis can be performed using automated instrumental analysis such as the YSI 2700 Select Biochemistry Analyzer available from YSI Incorporated, Yellow Springs, OH. A skilled artisan would also recognize that other automated or non-automated lactate analysis instruments or techniques can be used. Optical purity of L-lactic acid can be assessed via the techniques of circular dichroism (CD), HPLC using a chiral column or chiral resolving agent, or other manners known to the skilled artisan.

Identification of recovered L-lactic acid is made by comparison with pure standard (available, for example, Aldrich, Milwaukee, Wis.), using, for example, paper chromatography, thin-layer chromatography, gel permeation chromatography, elementary analysis, such as mass spectrometry, nuclear magnetic resonance spectroscopy, absorption spectroscopy or high-performance liquid chromatography (HPLC), or a combination thereof.

When L-lactic acid is recovered as a free acid, it can be converted to a salt, as desired, with sodium, potassium, calcium, ammonium or other cations as described herein or know to the skilled artisan using conventional methods. Alternatively, when L-lactic acid is recovered as a salt, it can be converted to its free form or to a different salt using conventional methods.

It is expected that the skilled artisan versed in the techniques of microbiology will be able to identify, isolate, alter via mutation, culture, and store, for example, the *Lactobacillus* strains or other bacterial strains which produce L-lactic acid as discussed herein. The following non-limiting examples illustrate various methods characteristic of the invention.

EXAMPLES

Example 1

The Enrichment and Isolation of Bacteria Producing L-lactic Acid from Dextrose in a Dextrose-Corn Steep Liquor Medium A 250 mL shaker flask containing 30 mL of enrichment medium (dextrose 100 g/L, ADM corn steep liquor 10 g/L as dry solid, calcium lactate 60-80 g/L, $MgSO_4 \cdot 7H_2O$ 0.6 g/L, $MnSO_4 \cdot H_2O$ 0.03 g/L, sodium acetate 1.0 g/L, $K_2HPO_4$ 0.5 g/L, $KH_2PO_4$ 0.5 g/L, $CaCO_3$ 50 g/L, pH adjusted to 6.5 before autoclaving) was inoculated with about 0.5 mL of a sample prepared from corn steep liquor or plant soil. This flask was shaken at 40° C. and 120 rpm for three days. The enriched culture was diluted and spread onto agar plates containing selective medium (glucose 60 g/L, ADM corn steep liquor 10 g/L as dry solid, calcium lactate 60-80 g/L, $MgSO_4 \cdot 7H_2O$ 0.6 g/L, $MnSO_4 \cdot H_2O$ 0.03 g/L, sodium acetate 1.0 g/L, $K_2HPO_4$ 0.5 g/L, $KH_2PO_4$ 0.5 g/L, Bromocresol green 0.02 g/L, agar 20 g/L, pH adjusted to pH 6.5). After incubating the plates at 40° C. for 3-5 days, colonies growing on the plates having a yellow halo were isolated and used to inoculate tubes containing 5 mL of the selective medium. Another small tube (0.6×4 cm) submerged in an upside down position in the selective medium was used to collect any gasses such as $CO_2$ produced by enriched culture. After 2-3 days incubation at 40° C., isolates which turned the blue color of the selective medium to yellow and produced no gas were selected for tests for their L-lactic acid production.

About 152 isolates were found to produce a significant amount of lactic acid (more than 30 g/L) in tubes containing 5 mL production medium A (dextrose 80 g/L, ADM corn steep liquor 10 g/L as dry solid, $MgSO_4 \cdot 7H_2O$ 0.6 g/L, $MnSO_4 \cdot H_2O$ 0.03 g/L, sodium acetate 1.0 g/L, $K_2HPO_4$ 0.5 g/L, $KH_2PO_4$ 0.5 g/L, $CaCO_3$ 50 g/L, pH adjusted to 6.5 before autoclaving). L-lactic acid production via shaker flask fermentation of some of these isolates is discussed in the next example.

Example 2

L-lactic Acid Produced by Isolated Bacteria in Shaker Flask Fermentation from a Dextrose-Corn Steep Liquor Medium A loopful of culture of an isolated bacterial strain growing on a Difco® MRS agar plate (Becton, Dickinson and Company, New Jersey) was inoculated into a 250 mL shaker flask containing 20 mL of seed medium A (dextrose 20 g/L, ADM corn steep liquor 30 g/L as dry solid, $MgSO_4 \cdot 7H_2O$ 0.2 g/L, $MnSO_4 \cdot H_2O$ 0.03 g/L, sodium acetate 1.0 g/L, $K_2HPO_4$ 0.6 g/L, $KH_2PO_4$ 0.6 g/L, $FeSO_4 \cdot 7H_2O$ 0.03 g/L, uracil 0.1 g/L, riboflavin 0.01 g/L, pH adjusted to 6.0 before autoclaving). The shaker flask culture was then incubated at 43° C. and 150 rpm on a rotary shaker. After 20 hours, 2 mL of seed culture was used to inoculate another 250 mL shaker flask containing 20 mL of production medium B (dextrose 100 g/L, ADM corn steep liquor 10 g/L as dry solid, $MgSO_4 \cdot 7H_2O$ 0.2 g/L, $MnSO_4 \cdot H_2O$ 0.03 g/L, sodium acetate 1.0 g/L, $K_2HPO_4$ 0.5 g/L, $KH_2PO_4$ 0.5 g/L, $FeSO_4 \cdot 7H_2O$ 0.03 g/L, $CaCO_3$ 67 g/L, pH adjusted to 6.0 before autoclaving). The production culture was then incubated at 43° C. and 150 rpm on a rotary shaker for 46-48 hours. Samples were analyzed using high pressure liquid chromatography (HPLC) for total lactic acid, % of L-lactic acid and dextrose. To determine the % of L-lactic acid, 10 μL of diluted sample was injected into an HPLC system with a pump capable of delivering 0.7 mL/minute through a Phenomenex (Torrance, Calif.) Chirax (D)-Penicillamine column (150×4.6 mm, 00F-3126-E0). Mobile phase is 0.5 g/L $CuSO_4$ with 25% methanol in Milli-Q™ purified water (Millipore, United States). Both L-lactic acid and D-lactic acid were separated and detected by a UV detector at 254 nm.

The lactic acid production of 130 isolates is summarized in Table 1 A. About 87% (or, 113 out of 130) of these isolates produced more then 60 g/L of lactic acid. Among them, the purity of L-lactic acid (given as a percentage of the total lactic acid) produced by these 113 strains is shown in Table 1 B. About 75% of these 113 isolates produced more than 96% of pure L-lactic acid.

TABLE 1

| L-lactic acid produced by isolated bacteria | | | | | | | |
|---|---|---|---|---|---|---|---|
| A. Total lactic acid (g/L) | less than 50 | 50 | 60 | 70 | 80 | 90 | 100 or more |
| Distribution of 130 isoplates | | | | | | | |
| Number | 11 | 6 | 39 | 40 | 23 | 7 | 4 |
| Percentage of Distribution | 8.46 | 4.62 | 30 | 30.77 | 17.69 | 5.38 | 3.08 |
| B. Purity of L-lactic acid (%) | less than 93 | 93 | 94 | 95 | 96 | 97 | 98 or more |
| Distribution of 113 isolates | | | | | | | |
| Number | 5 | 1 | 6 | 16 | 39 | 41 | 5 |
| Percentage of Distribution | 4.43 | 0.88 | 5.31 | 14.16 | 34.51 | 36.28 | 4.43 |

Example 3

Characterization of Six Isolated *Lactobacilli*

The biochemical profiles of bacterial strains including *Lactobacilli* can be characterized by observing their growth capability on carbohydrate-specific media. Such characterization is useful in strain identification and can be accomplished by monitoring culture growth in pre-prepared API 50 CHL medium (bioMérieux SA, France). In these culture growths, a cell suspension is made by innoculating a carbohydrate-specific medium with the microorganism to be tested. During incubation, carbohydrates are fermented to acids, which produce a decrease in pH, detected by the color change of an indicator present in the medium. The results make up the biochemical profiles of the tested strain and can be used in its identification.

Among those lactic acid producing bacteria described in Example 2, six gram positive, non-spore forming, catalase negative short rods were extensively studied. Biochemical and genetic analysis of these bacteria revealed that they belong to *Lactobacillus*. As shown in Table 2, their capability to use 49 carbohydrates has been examined from their growth on API 50 CHL medium. Biochemical profiles of the above mentioned six isolates suggested a relationship to *L. rhamnosus* or *L. para.paracasei*. Hence, the genetics of these isolates were compared with *L. rhamnosus* ATCC 7469 and *L. paracasei* sub *paracasei* ATCC 27216 using RiboPrinter® Microbial Characterization System (Qualicon Inc., Delaware). However, as shown in FIG. 1, restriction analysis reveals that these isolates are not genetically close to the two ATCC strains. Among these six isolates, NRRL B-30568 (ADM B6-4) and NRRL B-30572 (ADM RP3-1E) showed their close relation to each other on both biochemical and genetic characterization. Similarities were also found between NRRL B-30570 (ADM RP1A-4E) and NRRL B-30573 (ADM RP4A-2C).

TABLE 2

The biochemical profiles of six isolated *Lactobacilli*

| Carbohydrates | B6-4 NRRL B-30568 | DEC2-2B NRRL B-30569 | RP2-1C NRRL B-30571 | RP3-1E NRRL B-30572 | RP1A-4E NRRL B-30570 | RP4A-2C NRRL B-30573 |
|---|---|---|---|---|---|---|
| Glycerol | − | − | − | − | − | − |
| Erythritol | − | − | − | − | − | − |
| D-arabinose | − | + | − | − | − | − |
| L-arabinose | + | + | − | − | − | − |
| Ribose | + | + | + | + | + | + |
| D-xylose | − | − | − | − | − | − |
| L-xylose | − | − | − | − | − | − |
| Adonitol | − | − | + | − | + | + |
| Beta-methyl-D-xyloside | − | − | − | − | − | − |
| Galactose | + | + | + | + | + | + |
| Glucose | + | + | + | + | + | + |
| Fructose | + | + | + | + | + | + |
| Manose | + | + | + | + | + | + |
| Sorbose | − | − | + | − | − | − |
| Rhamnose | − | + | + | − | + | + |
| Dulcitol | + | + | + | + | − | − |
| Inositol | + | + | + | + | + | + |
| Mannitol | + | + | + | + | + | + |
| Sorbitol | + | + | + | + | + | + |
| Alpha-methyl-D-mannoside | − | − | − | − | − | − |
| Alpha-methyl-D-glucoside | + | − | + | + | − | − |
| N-acetyl-glucosamine | + | + | + | + | + | + |
| Amygdalin | + | + | + | + | + | + |
| Arbutin | + | + | + | + | + | + |
| Esculin | + | + | + | + | + | + |
| Salicin | + | + | + | + | + | + |
| Cellobiose | + | + | + | + | + | + |
| Maltose | + | + | + | + | + | + |
| Lactose | + | + | + | + | + | + |
| Melibiose | + | − | − | − | − | − |
| Sucrose | + | − | + | + | − | − |
| Trehalose | + | + | + | + | + | + |
| Imulin | − | − | − | − | − | − |
| Melezitose | + | + | + | + | + | + |
| Raffinose | − | − | − | − | − | − |
| Starch | + | − | − | + | − | − |
| Glycogen | − | − | − | − | − | − |
| Xylitol | − | − | − | − | − | − |
| Gentiobiose | + | − | + | + | + | − |
| D-turanose | + | − | + | + | − | − |
| D-lyxose | − | − | − | − | − | − |
| D-tagatose | + | + | + | + | + | + |
| D-Fucose | − | − | − | − | − | − |
| L-fucose | − | + | + | − | − | − |
| D-arabitol | − | − | − | − | − | − |
| L-arabitol | − | − | − | − | − | − |
| Gluconate | + | + | + | + | − | − |
| 2-keto-gluconate | − | − | − | − | − | − |
| 5-keto-gluconate | − | − | − | − | − | − |

+: growth;
−: no growth

Example 4

The Lactic Acid Produced by Six Solates in Fermentors

Frozen cultures were prepared by growing each isolated *Lactobacillus* strain in a 250 mL flask containing 20 mL of Difco® Lactobacilli MRS Broth (Becton, Dickinson and Company, New Jersey) and incubating overnight on a shaker at 43° C. and 150 rpm. Sterile glycerol to a final concentration of 15% was added to aliquots of the overnight cultures, mixed, and stored at −72° C. in a deep freezer in 2 mL cryogenic vials. To test these cultures, a vial of each was removed from the freezer and thawed. 0.5 mL of thawed culture was used to inoculate 100 mL of seed medium A (as described in Example 2) in a 500 mL flask. The medium was incubated on a shaker at 150 rpm at 43° C. for 20 hours. The seed medium was then used to inoculate 1000 mL of production medium C (dextrose 130 g/L, sodium acetate 1 g/L, ADM corn steep liquor 10 g/L as dry solid, riboflavin 0.001 g/L, $MgSO_4 \cdot 7H_2O$ 0.2 g/L, $MnSO_4 \cdot H_2O$ 0.03 g/L, $FeSO_4 \cdot 7H_2O$ 0.03 g/L $K_2HPO_4$ 0.5 g/L, $KH_2PO_4$ 0.5 g/L, $CaCO_3$ 75 g/L, antifoam 6000K 0.2 mL/L, pH adjusted to 6.0) in a 1.5 L fermentor. The fermentation was controlled with the following conditions: temperature=43° C.; air=0.05 vvm; agitation=250 rpm. After 50 hours, samples were analyzed with HPLC and a YSI automated lactate analyzers for lactic acid and dextrose. The L-lactic acid production of these isolated *Lactobacilli* is summarized in Table 3. All of the isolates produced high concentrations of L-lactic acid in fermentors from the dextrose-corn steep medium (medium C). Based on its higher yield % and chiral purity of L-lactic acid production, strain NRRL B-30568 (ADM B6-4) was selected for the development of improved L-lactic acid producing strains.

$KH_2PO_4$ 0.6 g/L, calcium lactate 120 g/L, agar 20 g/L, pH 6.0). Mutants growing on LPM agar plates were isolated and screened for their L-lactic acid production through micro plate and shaker flask fermentation.

To analyze D-lactic acid production of mutants, colonies isolated from LPM plates were transferred to Difco® MRS agar micro plates and incubated at 43° C. for 1-2 days. Colonies on these MRS micro plates were then replica inoculated into a second set of micro plates containing 250 μL/well of MRS broth. After incubating the broth on a shaker at 43° C. and 120 rpm for 24 hours, this second set of micro plates was removed and heated at 75° C. in an incubator oven for 1 hour. Exactly 20 microliters of heated micro plate culture (in broth) from each well of the second set of micro plates were transferred into a third set of micro plates containing 180 μL/well of reaction solution [HEPES 50 mM at pH 7.5, beta-nicotinamide adenine dinucleotide (AND) 0.5 mM, diaphorase 0.1 unit, 2,6-dichloroindophenol (DPIP) 0.06 mM, D-lactate dehydrogenase (D-LDH) 1 unit].

The reaction as shown above will start immediately at room temperature and finish within minutes. The blue color

TABLE 3

The L-lactic acid production of isolated *Lactobacilli* in fermentors

| Strain | B6-4 NRRL B-30568 | DEC2-2B NRRL B30569 | RP1A-4E NRRL B-30570 | RP2-1C NRRL B-30571 | RP3-1E NRRL B-30572 | RP4A-2C NRRL B-30573 |
|---|---|---|---|---|---|---|
| Lactic acid (g/L) | 84.8 | 86.7 | 86.7 | 83.1 | 86.2 | 87.7 |
| Yield (%) | 98 | 84 | 86 | 81 | 85 | 95 |
| L-Lactic acid (%) | 98.1 | 96.4 | 96.8 | 97.3 | 96.9 | 97.2 |

Example 5

Mutagenesis and Selection for Mutants Producing 100% Pure L-Lactic Acid

The creation and selection of mutant B6-4 strains having improved L-lactic acid yield and optical purity proceeded according to the following. Mid-log culture growing in Difco® Lactobacilli MRS Broth was harvested and the collected cells were suspended in TM buffer (Tris.HCl 6.0 g/L, maleic acid 5.8 g/L, $(NH_4)_2SO_4$ 1.0 g/L, $Ca(NO_3)_2$ 5 mg/L, $MgSO_4 \cdot 7H_2O$ 0.1 g/L, $FeSO_4 \cdot 7H_2O$ 0.25 mg/L, adjusted to pH 6.0 using KOH). The culture was then treated with 100 μg/mL of N-methyl-N-nitro-N-nitrosoguanidine (NTG) and incubated at 43° C. for 40 minutes. The mutagenesis was stopped by washing the cells several times with TM buffer and then suspending the treated culture in 0.1 M phosphate buffer (pH 7.0).

The mutagenized culture was then spread onto agar plates containing *Lactobacillus* agar plate medium (LPM: dextrose 5 g/L, sodium acetate 1 g/L, ADM corn steep liquor 10 g/L as dry solid, $MgSO_4 \cdot 7H_2O$ 0.6 g/L, $MnSO_4 \cdot H_2O$ 0.03 g/L, of DPIP can be stable for several hours. The sensitivity of this microassay is in the range of 0.001-0.01% D-lactate. After 30 minutes, the optical density of the reaction in the third set of micro plates was measured with a micro plate reader at 600 nm. Mutants producing the least amount of D-lactate gave the highest reading at 600 nm.

Figure 2:
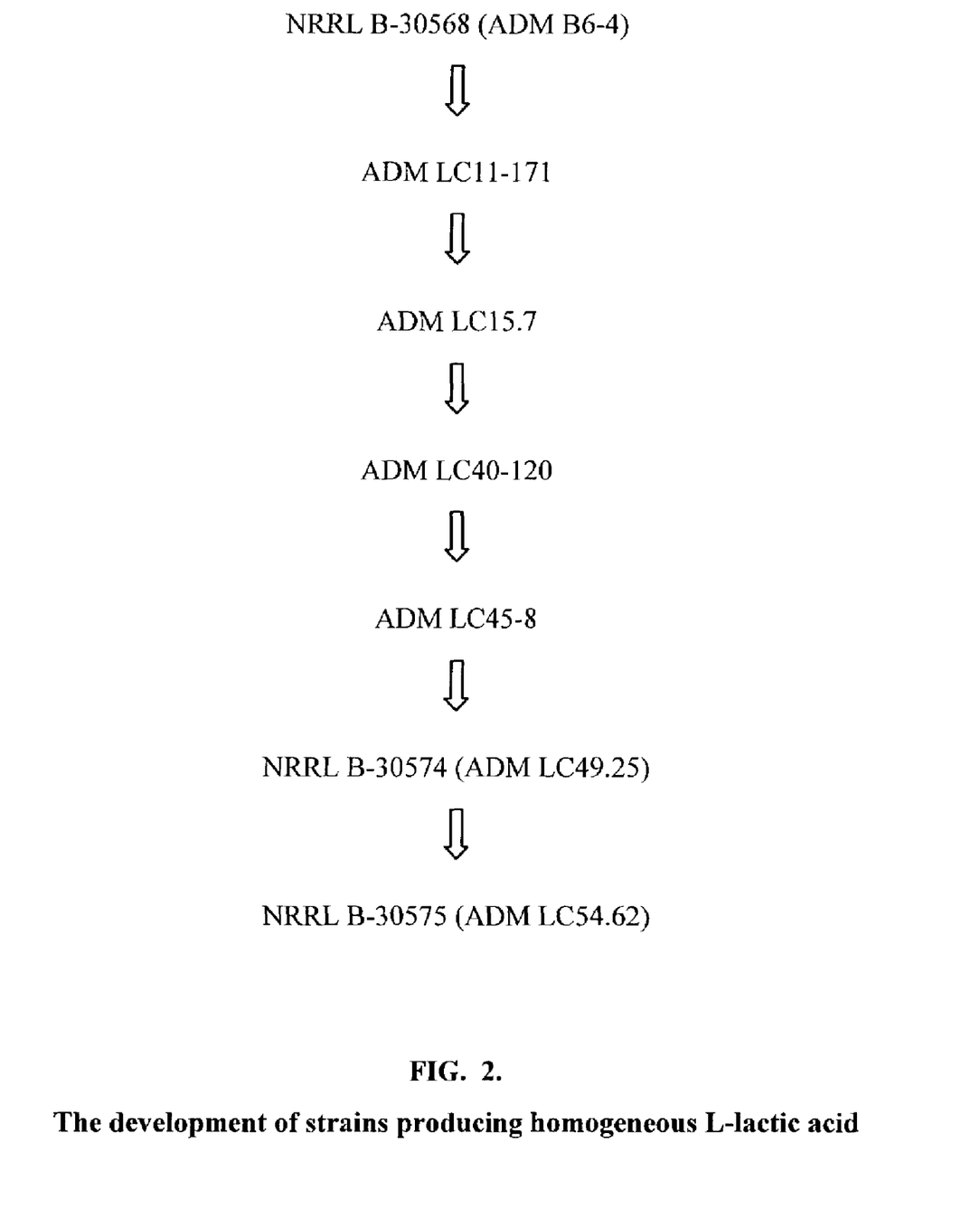
FIG. 2 is a depiction of the development of strains producing homogeneous L-lactic acid. Serial mutations beginning with NRRL B-30568 (ADM B6-4) led to NRRL B-30575 (ADM LC54.62).

These mutants were then selected for further tests for their D,L-lactic acid production in shaker flasks and fermentors. Mutants producing homogeneous L-lactic acid were selected through these processes. The development of strain NRRL B-30568 (ADM B6-4) and its mutant variants is depicted in FIG. 2.

Example 6

The Production of L-lactic Acid by Mutants Developed from NRRL B-30568 (ADM B6-4)

Through several cycles of mutagenesis and selection using micro plate and flask screening as described in the previous examples, mutants that produce only L-lactic acid were isolated for tests in fermentors. It was found that about 0.5-1 g/L of D-lactic acid in production medium A, B, or C used in this invention came from ADM corn steep liquor in ingredients. To demonstrate isolated mutants making pure L-lactic acid, both seed and production media have been modified to replace ADM corn steep liquor with ADM Nutrisoy® (soy flour) and Red Star Tastone® (yeast extract).

About 0.5 mL of culture thawed from a frozen vial as described in Example 4 was inoculated into 100 mL of seed medium B (dextrose 20 g/L, Tastone® 5 g/L, Nutrisoy® 5 g/L, $MgSO_4 \cdot 7H_2O$ 0.2 g/L, $MnSO_4 \cdot H_2O$ 0.03 g/L, sodium acetate 1.0 g/L, $K_2HPO_4$ 0.6 g/L, $KH_2PO_4$ 0.6 g/L, $FeSO_4 \cdot 7H_2O$ 0.03 g/L, uracil 0.1 g/L, riboflavin 0.01 g/L, pH adjusted to 6.0 before autoclaving) in a 500 mL flask. Cultures were incubated on a shaker at a 150 rpm and 43° C. After 20 hours, seeds were transferred to fermentors containing 1 L of production media D (dextrose 130 g/L, sodium acetate 1 g/L, Tastone® 5 g/L, Nutrisoy® 5 g/L, riboflavin 0.001 g/L, $MgSO_4 \cdot 7H_2O$ 0.2 g/L, $MnSO_4 \cdot H_2O$ 0.03 g/L, $FeSO_4 19 \, 7H_2O$ 0.03 g/L $K_2HPO_4$ 0.5 g/L, $KH_2PO_4$ 0.5 g/L, $CaCO_3$ 75 g/L, antifoam 6000K 0.2 mL/L, pH adjusted to 6.0). The fermentation was controlled under the following conditions: temperature=43° C.; air=0.05 vvm; agitation=250 rpm. After 45 hours, samples were analyzed with HPLC and a YSI automated lactate analyzer for lactic acid and dextrose. As shown in Table 4, the production of homogeneous L-lactic acid has been improved through the mutagenesis and screening approach described in Example 5. In these cultures, almost 100% pure L-lactic acid has been produced by mutants NRRL B-30574 (ADM LC49.25) and NRRL B-30575 (ADM LC 54.62).

TABLE 4

Production of L-lactic acid by mutants derived from strain ADM B6-4

| Strain | B6-4 NRRL B-30568 | LC45.8 | LC49.25 NRRL B-30574 | LC54.62 NRRL B-30575 |
|---|---|---|---|---|
| Total lactic acid (g) | 105.25 | 106.41 | 109.96 | 98.83 |
| Purity of L-lactic acid (%) | 98.39 | 99.49 | 99.77 | 99.98 |

During subsequent tests, NRRL B-30574 (ADM LC49.25) produced 100% of L-lactic acid in fermentors using the same media with several different concentrations of Tastone® and Nutrisoy® (See Table 5). In these culture growths, the same conditions (temperature, aeration and agitation) and seed media B were used as described for the tests resulting in Table 4. However, different concentrations of Tastone® and Nutrisoy® were used in production media D, with the other ingredients remaining the same. The fermentation time for these subsequent tests was 50 hours. Lower concentrations of Tastone® and Nutrisoy® could not provide the culture with enough nutrients and resulted in poor growth and lower production of L-lactic acid.

TABLE 5

Production of L-lactic acid by NRRL B-30574 (ADM LC249.25) at different concentrations of Tastone ® and Nutrisoy ®

| Tastone ® (g/L) and Nutrisoy ® (g/L) | 5 | 4 | 3 | 2 | 1 | 0.5 |
|---|---|---|---|---|---|---|
| | 5 | 4 | 3 | 2 | 1 | 0.5 |
| Total lactic acid (g) | 102.7 | 91.4 | 82.6 | 70.5 | 41.9 | 20.3 |
| Purity of L-lactic acid (%) | 100 | 100 | 100 | 100 | 100 | 100 |

All publications mentioned herein above are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated bacterial strain selected from the group consisting of NRRL B-30568 (ADM B6-4), NRRL B-30569 (ADM DEC2-2B), NRRL B-30570 (ADM RP1A-4E), NRRL B-30571 (ADM RP2-1C), NRRL B-30572 (ADM RP3-1E), NRRL B-30573 (ADM RP4A-2C), NRRL B-30574 (ADM LC49.25), and NRRL B-30575 (ADM LC54.62).

2. A bacterial culture comprising the isolated bacterial strain of claim 1.

3. The isolated bacterial strain of claim 1, wherein the isolated bacterial strain is NRRL B-30568 (ADM B6-4).

4. A bacterial culture comprising the isolated bacterial strain of claim 3.

5. The isolated bacterial strain of claim 1, wherein the isolated bacterial strain is NRRL B-30569 (ADM DEC2-2B).

6. A bacterial culture comprising the isolated bacterial strain of claim 5.

7. The isolated bacterial strain of claim 1, wherein the isolated bacterial strain is NRRL B-30570 (ADM RP1A-4E).

8. A bacterial culture comprising the isolated bacterial strain of claim 7.

9. The isolated bacterial strain of claim 1, wherein the isolated bacterial strain is NRRL B-30571 (ADM RP2-1C).

10. A bacterial culture comprising the isolated bacterial strain of claim 9.

11. The isolated bacterial strain of claim 1, wherein the isolated bacterial strain is NRRL B-30572 (ADM RP3-1E).

12. A bacterial culture comprising the isolated bacterial strain of claim 11.

13. The isolated bacterial strain of claim 1, wherein the isolated bacterial strain is NRRL B-30573 (ADM RP4A-2C).

14. A bacterial culture comprising the isolated bacterial strain of claim 13.

15. The isolated bacterial strain of claim 1, wherein the isolated bacterial strain is NRRL B-30574 (ADM LC49.25).

16. A bacterial culture comprising the isolated bacterial strain of claim 15.

17. The isolated bacterial strain of claim 1, wherein isolated bacterial strain is NRRL B-30575 (ADM LC54.62).

18. A bacterial culture comprising the isolated bacterial strain of claim 17.

* * * * *